United States Patent
Dai et al.

(10) Patent No.: US 10,028,862 B2
(45) Date of Patent: Jul. 24, 2018

(54) COMPENSATION SYSTEMS AND METHODS FOR FLAP INDUCED ABERRATIONS

(71) Applicant: AMO Development, LLC, Santa Ana, CA (US)

(72) Inventors: Guang-ming Dai, Fremont, CA (US); Anatoly Fabrikant, Fremont, CA (US); Stanley S. Bentow, Laguna Hills, CA (US)

(73) Assignee: AMO Development, LLC, Santa Ana, CA (US)

( * ) Notice: Subject to any disclaimer, the term of this patent is extended or adjusted under 35 U.S.C. 154(b) by 1029 days.

(21) Appl. No.: 14/097,841

(22) Filed: Dec. 5, 2013

(65) Prior Publication Data

US 2014/0163535 A1 Jun. 12, 2014

Related U.S. Application Data

(60) Provisional application No. 61/734,030, filed on Dec. 6, 2012.

(51) Int. Cl.
*A61F 9/008* (2006.01)

(52) U.S. Cl.
CPC .. *A61F 9/00806* (2013.01); *A61F 2009/0088* (2013.01); *A61F 2009/00844* (2013.01); *A61F 2009/00848* (2013.01); *A61F 2009/00859* (2013.01); *A61F 2009/00872* (2013.01)

(58) Field of Classification Search
CPC ........ A61F 9/00806; A61F 2009/00844; A61F 2009/00848; A61F 2009/00859; A61F 2009/00872; A61F 2009/0088
USPC ............................................................ 606/5
See application file for complete search history.

(56) References Cited

U.S. PATENT DOCUMENTS

| | | |
|---|---|---|
| 5,891,132 A | 4/1999 | Hohla |
| 6,090,100 A | 7/2000 | Hohla |
| 6,428,533 B1 * | 8/2002 | Bille ................... A61B 3/1015 606/11 |
| 7,044,602 B2 | 5/2006 | Chernyak |
| 7,391,887 B2 | 6/2008 | Durnell |
| 7,926,490 B2 | 4/2011 | Dai et al. |
| 2002/0082629 A1 * | 6/2002 | Cox ........................ A61F 9/008 606/166 |
| 2004/0233387 A1 | 11/2004 | Huang et al. |
| 2005/0096640 A1 * | 5/2005 | Dai ......................... A61F 9/008 606/10 |
| 2005/0107775 A1 | 5/2005 | Huang et al. |
| 2006/0173445 A1 * | 8/2006 | Bille ................... A61B 3/1015 606/5 |

(Continued)

OTHER PUBLICATIONS

Durrie, D.S., Kezirian, G.M., "Femtosecond laser versus mechanical keratome flaps in wavefront-guided laser in situ keratomileusis: Prospective contralateral eye study." *Journal of Cataract and Refractive Surgery* vol. 31, No. 1, (2005): pp. 120-126.

(Continued)

*Primary Examiner* — Lynsey Eiseman
(74) *Attorney, Agent, or Firm* — Johnson & Johnson Surgical Vision, Inc.

(57) ABSTRACT

Embodiments of the present invention encompass systems and methods for customized vision treatments that account for effects associated with corneal flap creation.

11 Claims, 10 Drawing Sheets

(56) References Cited

U.S. PATENT DOCUMENTS

2013/0190736 A1* 7/2013 Fabrikant ............ A61F 9/00804
606/5
2014/0095137 A1 4/2014 Dai et al.
2015/0066466 A1 3/2015 Chernyak et al.

OTHER PUBLICATIONS

Pallikaris, I.G., et al., "Induced optical aberrations following formation of a laser in situ keratomileusis flap." *Journal of Cataract and Refractive Surgery* vol. 28 (2002): pp. 1737-1741.
Porter, J., et al., "Separate Effects of the Microkeratome Incision and Laser Ablation on the Eye's Wave Aberration." *American Journal of Ophthalmology* vol. 136, No. 2 (2003): pp. 327-337.
Tran, D.B., et al., "Randomized prospective clinical study comparing induced aberrations with IntraLase and Hansatome flap creation in fellow eyes: Potential impact on wavefront-guided laser in situ keratomileusis." *Journal of Cataract and Refractive Surgery* vol. 31 (2005): pp. 97-105.
Richard J. Kolker, MD, "Sunjecting Refraction and Prescribing Glasses", Nov. 2014, 82 pages.
W.J.B. Riddell, "A Note on the Spherical Equivalent of Sphero-Cylindrical Lenses", 3 pages.
M. Vilaseca et al., "Optics of Astigmatism and Retinal Image Quality", 26 pages.

* cited by examiner

COMPENSATION SYSTEMS AND METHODS FOR FLAP INDUCED ABERRATIONS

CROSS-REFERENCES TO RELATED APPLICATIONS

This application is a nonprovisional of and claims the benefit of priority to U.S. Provisional Patent Application No. 61/734,030 filed Dec. 6, 2013. This application is also related to U.S. patent application No. 61/708,815 and Ser. No. 14/044,650 filed Oct. 2, 2012 and Oct. 2, 2013, respectively. The entire content of each of the above filing is incorporated herein by reference for all purposes.

BACKGROUND OF THE INVENTION

Embodiments of the present invention relate generally to vision treatment, and in particular to treatment systems and methods that provide for site specific adjustment of post-operative induced aberrations in Laser Assisted In-Situ Keratomileusis (LASIK) refractive surgery.

Corneal shape corrective surgeries are commonly used to treat myopia, hyperopia, astigmatism, and the like. During LASIK, a suction ring is typically placed over sclera tissue (the white part of the eye) to hold the eye firmly. A surgeon first uses a microkeratome with an oscillating steel blade to make a partial cut through a front surface of a cornea. A microkeratome automatically passing across a cornea creates a thin flap of clear tissue on a front central part of an eye. A suction ring is then removed, and a flap is lifted back to sufficiently expose tissue for ablation with a laser. A laser is programmed to correct a desired amount of visual effect, and directs a laser beam. A rapid, continuous emission of laser pulses removes very small precise amounts of corneal tissue. After irrigation with saline solution, a corneal flap is folded back to adhere to its original position. As discussed elsewhere herein, any of a variety of instruments or techniques can be used to create a corneal flap.

Although vision treatment techniques that include the creation of a flap provide real benefits to patients in need thereof, still further improvements are desirable. Embodiments of the present invention provide solutions for at least some of these outstanding needs.

BRIEF SUMMARY OF THE INVENTION

Corneal flap creation during the LASIK refractive surgery may induce changes in corneal refraction as well as in high-order aberrations, including spherical aberration (SA), coma, trefoil, or the like. These aberrations can affect the LASIK outcome and can be taken into account for treatment planning. According to some embodiments, deconvolution techniques involve the removal or reduction of surgically induced aberrations, such as spherical aberration induced during LASIK treatment.

Certain embodiments enable customized treatment planning based on flap induced aberrations. For example, it is possible to use factors which are specific to a particular site, such as the identity of a surgeon, treatment tools used, treatment conditions, or the like, to obtain a customized treatment. Hence, a custom determination of flap induced aberrations can be based on a statistical estimation where a customized aspect involves using the site specific factors. These factors can be used to determine or adjust a vision treatment plan.

Embodiments of the present invention encompass systems and methods that involve combining adjusted treatment data from different sites and/or surgeons for a representative statistical analysis leading to a precise treatment planning.

Each surgeon may use their own nomogram and physician adjustments to compensate for post-operative refractive errors. These adjustments are derived from statistics of post-treatment data. The physician adjustment may compensate for the site-specific and/or the flap-induced SE.

According to some embodiments, corneal flap creation during the LASIK surgery induces changes in refraction and high-order aberrations, which can be taken into account for treatment planning. The flap-induced aberration, which may not depend on the ablation magnitude, may be different for different surgeons, different tools, of different sites. The flap-induced aberrations can be estimated, and the estimates used to adjust the treatment target accordingly. Flap-induced aberrations can be measured directly, when the flap is placed back with no ablation performed. Flap-induced aberrations can also be estimated statistically. For instance, the trend line of induced spherical aberration (SA) vs. pre-operative spherical equivalent (SE) can cross the axis SE=0 at some non-zero level. This value can quantify the change in SA when only the flap is created, but no corrective ablation is performed. Flap-induced aberrations can also be derived from a flap-creation model, which takes into account site-specific parameters. The value may depend on multiple factors, including the difference for the flap creation with a mechanical microkeratome vs. a femto-second laser, individual surgeon techniques, operating environment, and the like. Statistics of flap-induced SA calculated with data from controlled clinical studies showing significant differences between different operating sites are discussed elsewhere herein. Flap-induced aberrations may be taken into account during the treatment planning, when treatment target adjustment is applied to compensate for these aberrations. The adjustments may be derived statistically for each site, surgeon, or tool. The site-specific $SA_0$ can be readjusted such that the adjusted scatter plot will become more compact with increased correlation and R2 values. This can allow a better fit for the nomogram adjustment as well as more precise modeling of the cornea healing. Hence, flap-induced aberrations for LASIK treatments may substantially contribute to the surgery outcome. The magnitude of aberrations can be different for different surgeons, sites, or tools, and can be estimated for each surgeon individually. Data for different surgeons can be combined for subsequent analysis and adjustments.

In one aspect, embodiments of the present invention encompass systems and methods for generating a vision treatment protocol for a patient. Exemplary vision treatment protocol generation methods include obtaining a flap induced aberration parameter that corresponds to a specific treatment site, and generating the vision treatment protocol based on the flap induced aberration parameter. In some cases, the flap induced aberration parameter includes a high order aberration. In some cases, the high order aberration includes a spherical aberration. Some methods further include delivering the vision treatment protocol to the patient.

In another aspect, systems and methods for generating a vision treatment for a patient may involve obtaining a low order flap induced aberration parameter that corresponds to a specific treatment site, surgeon, or refractive type, and generating the vision treatment protocol based on the low order flap induced aberration parameter. In some cases, the low order flap induced aberration parameter includes a spherical equivalent. Some methods may further include delivering the vision treatment protocol to the patient.

In still another aspect, systems for generating a vision treatment protocol for a patient may include a processor, a first module, and a second module. The first module may include a tangible medium embodying machine-readable code executed on the processor to obtain a flap induced aberration parameter that corresponds to a specific treatment site. The second module may include a tangible medium embodying machine-readable code executed on the processor to generate the vision treatment protocol based on the flap induced aberration parameter. In some cases, the flap induced aberration parameter is a high order aberration. In some cases, the high order aberration is a spherical aberration. Systems may also include a vision treatment protocol delivery module having a tangible medium embodying machine-readable code executed on the processor to deliver the vision treatment protocol to the patient. In some cases, the vision treatment protocol includes a laser treatment.

In yet another aspect, systems for generating a vision treatment protocol for a patient can include a processor, a first module having a tangible medium embodying machine-readable code executed on the processor to obtain a low order flap induced aberration parameter that corresponds to a specific treatment site, surgeon, or refractive type, and a second module having a tangible medium embodying machine-readable code executed on the processor to generate the vision treatment protocol based on the low order flap induced aberration parameter. In some cases, the low order flap induced aberration parameter is a spherical equivalent. Systems can also include a vision treatment protocol delivery module having a tangible medium embodying machine-readable code executed on the processor to deliver the vision treatment protocol to the patient. The vision treatment protocol can include a laser treatment.

In still yet another aspect, embodiments of the present invention encompass a computer product embodied on a tangible computer readable storage medium, where the computer product includes code for obtaining a flap induced aberration parameter that corresponds to a specific treatment site, and code for generating the vision treatment protocol based on the flap induced aberration parameter. Computer products can further include code for administering the vision treatment protocol to the eye of the patient.

In another aspect, embodiments of the present invention encompass a computer product embodied on a tangible computer readable storage medium, where the computer product includes code for obtaining a low order flap induced aberration parameter that corresponds to a specific treatment site, surgeon, or refractive type, and code for generating the vision treatment protocol based on the low order flap induced aberration parameter. A computer product can also include code for administering the vision treatment protocol to the eye of the patient.

In another aspect, embodiments of the present invention encompass systems and methods for combining adjusted treatment data from different sites and/or surgeons for a representative statistical analysis leading to a precise treatment planning.

DETAILED DESCRIPTION OF THE INVENTION

Corneal flap creation during a LASIK surgery can induce changes in refraction and high-order aberrations. Embodiments of the present invention involve taking these effects into account for treatment planning purposes. These flap induced changes may overlap with subsequent induced aberrations that are related to post-operative corneal healing.

In some instances, a flap-induced aberration does not depend on the ablation magnitude, and may be different for different surgeons, different tools, and/or different sites. In some cases, the ablation magnitude can be defined as a depth (e.g. the maximum depth) of the ablation profile. According to certain embodiments of the present invention, it is possible to estimate the flap-induced aberrations and use these estimates to adjust the treatment target.

Embodiments of the present invention can be readily adapted for use with existing laser systems and other optical treatment devices. Although system, software, and method embodiments of the present invention are described primarily in the context of a laser eye surgery system, it should be understood that embodiments of the present invention may be adapted for use in or in combination with alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom preformed lenses, intraocular lenses, custom contact lenses, custom corneal implants, and the like, which can be configured to treat or ameliorate any of a variety of vision conditions in a particular patient based on their unique ocular characteristics or anatomy. Additionally, the modified ablation target or target shape may be implemented via other non-ablative laser therapies, such as laser-incised custom lenticule shapes and subsequent extraction and laser-based corneal incision patterns.

In some instances, these techniques can be carried out in conjunction with treatments provided by any of a variety of laser devices, including without limitation the WaveScan® System and the STAR S4® Excimer Laser System both by Abbott Medical Optics Inc., the WaveLight® Allegretto Wave® Eye-Q laser, the Schwind Amaris™ lasers, the 217P excimer workstation by Technolas PerfectVision GmbH, the Mel 80™ laser by Carl Zeiss Meditec, Inc., and the like. In some cases, embodiments provide techniques for using laser basis data during refractive surgery treatment procedures which can be implemented in such laser devices.

Figure 1:
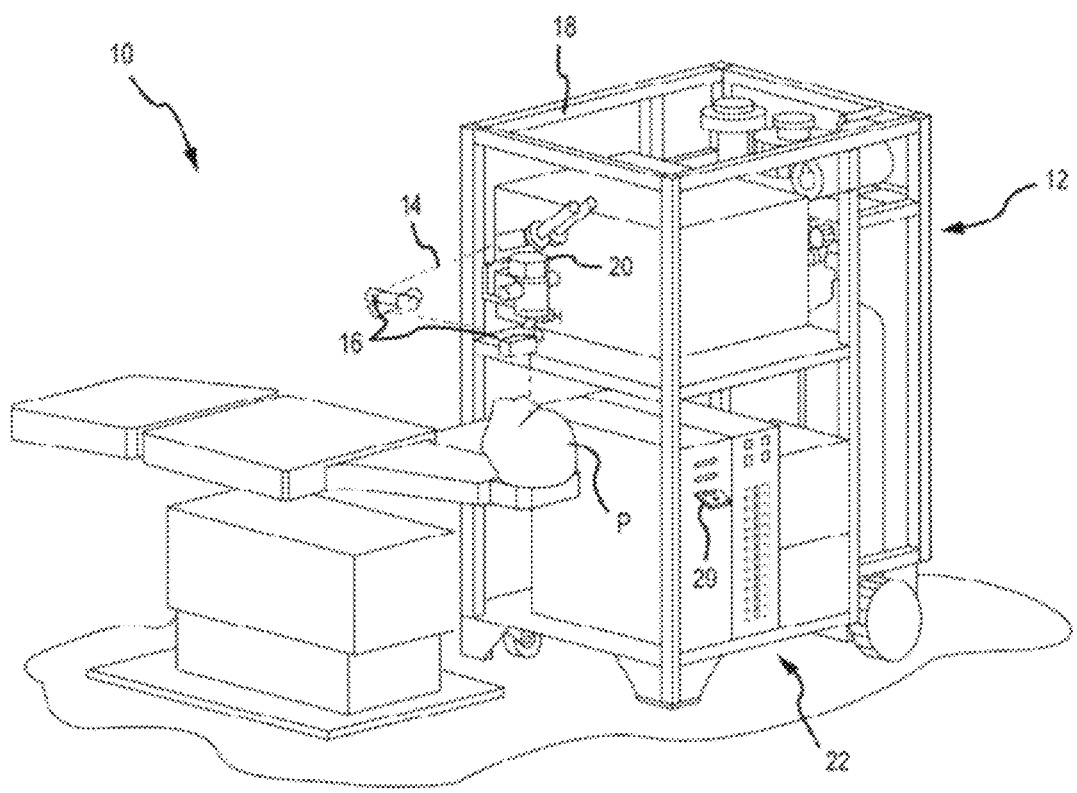
FIG. 1 illustrates a laser ablation system according to an embodiment of the present invention.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with an input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
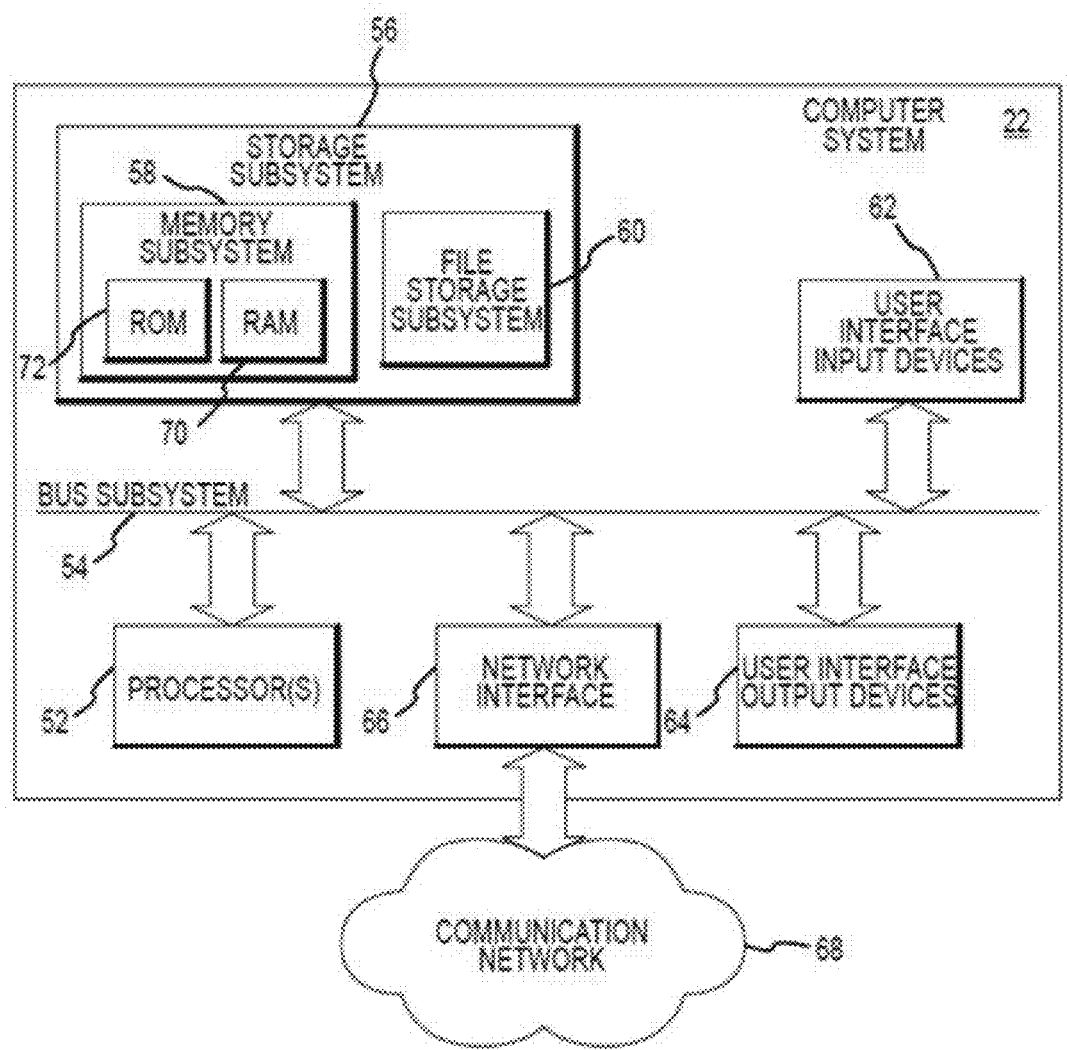
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
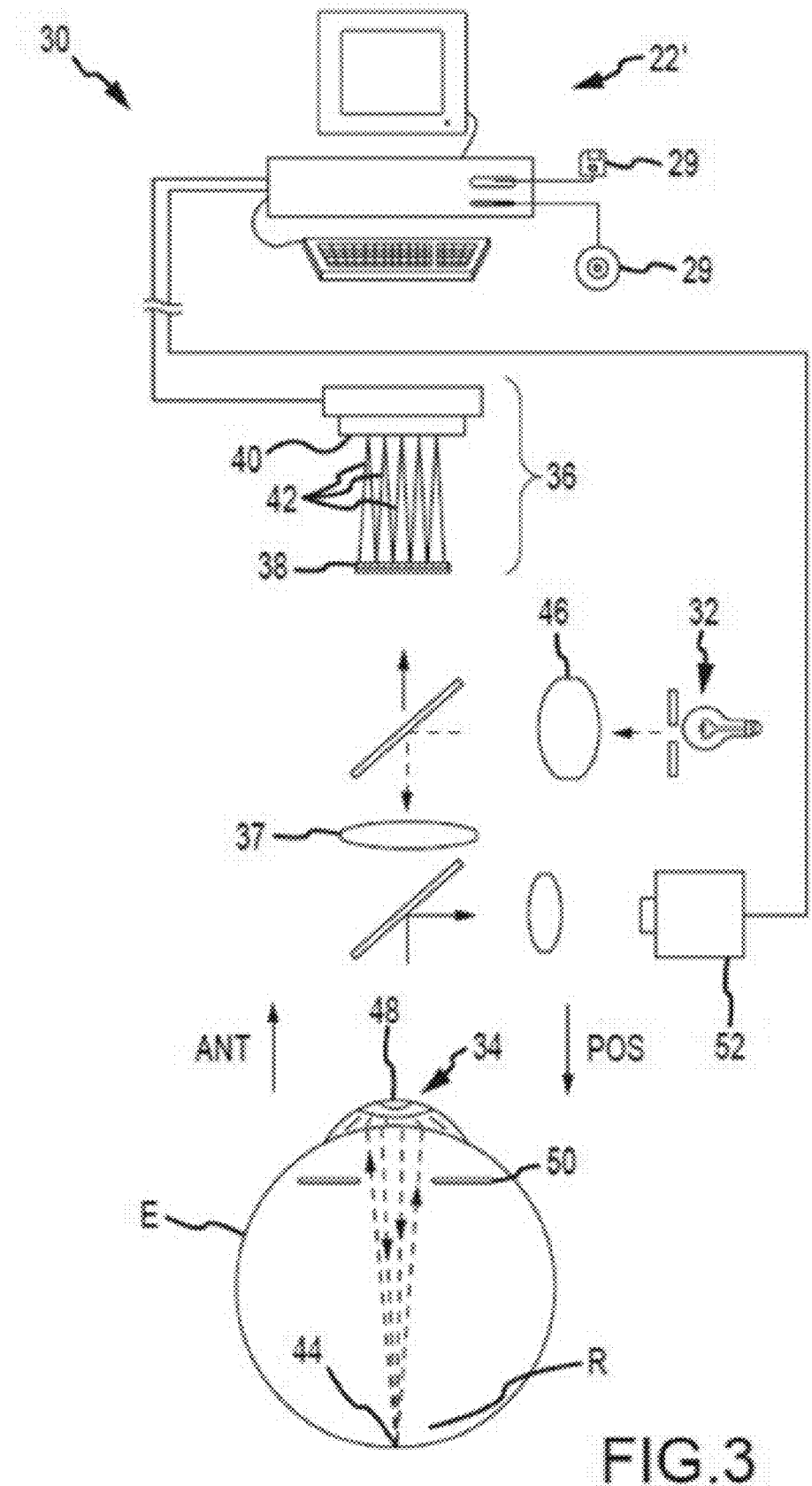
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
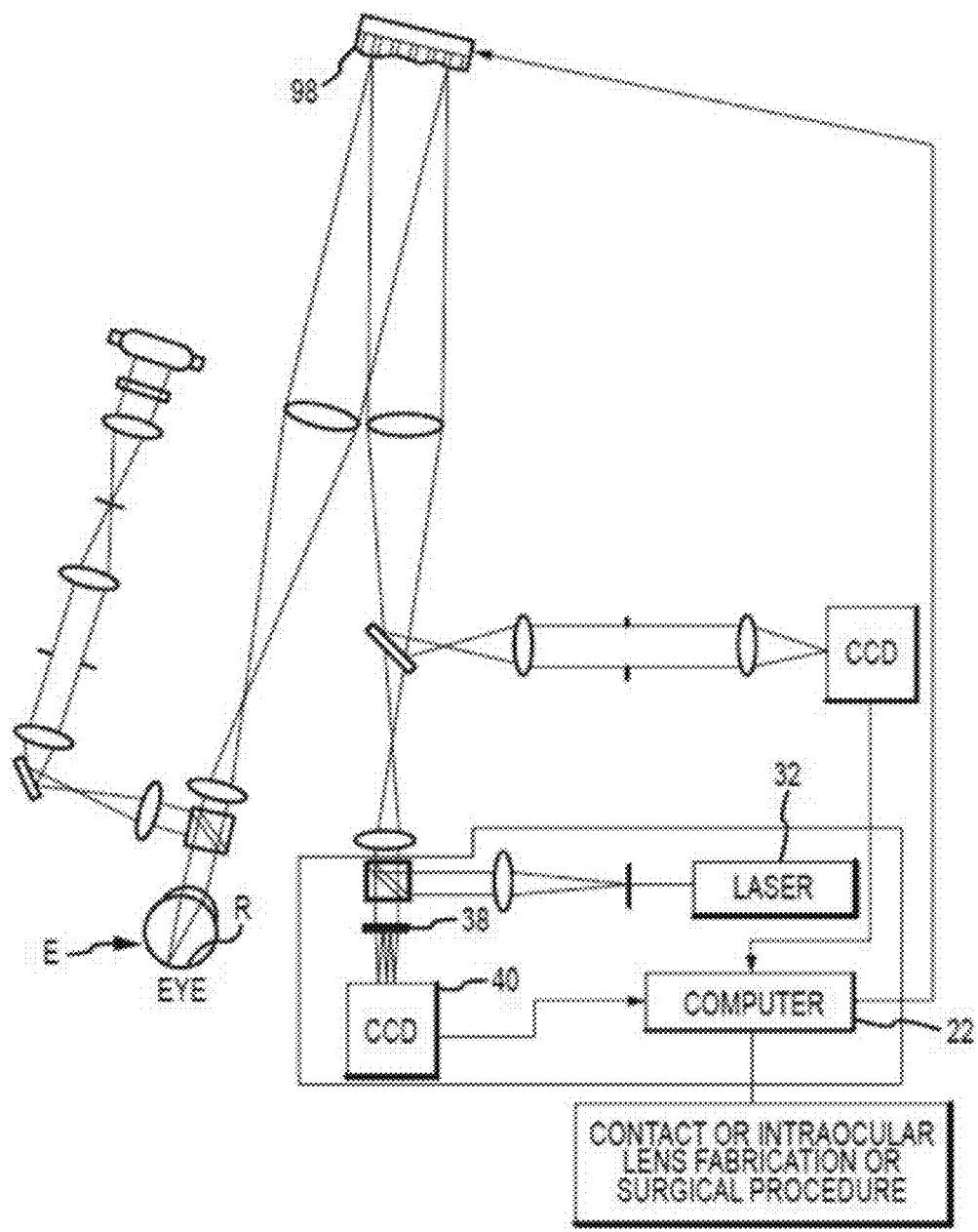
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from AMO MANUFACTURING USA, LLC, MILPITAS, Calif. One embodiment includes a WaveScan system with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention. Relatedly, embodiments of the present invention encompass the implementation of any of a variety of optical instruments provided by AMO WaveFront Sciences, LLC, including the COAS wavefront aberrometer, the ClearWave contact lens aberrometer, the CrystalWave IOL aberrometer, and the like.

Relatedly, embodiments of the present invention encompass the implementation of any of a variety of optical instruments provided by WaveFront Sciences, Inc., including the COAS wavefront aberrometer, the ClearWave contact lens aberrometer, the CrystalWave IOL aberrometer, and the like. Embodiments of the present invention may also involve wavefront measurement schemes such as a Tscherning-based system, which may be provided by WaveFront Sciences, Inc. Embodiments of the present invention may also involve wavefront measurement schemes such as a ray tracing-based system, which may be provided by Tracey Technologies, Corp.

Flap Creation and Induced Aberrations

Certain eye treatment modalities, such as LASIK refractive surgery, involve the creation of a corneal flap. Various instruments or techniques, including femtosecond lasers and microkeratome blades, can be used to create a flap in the tissue of the eye. Exemplary flap creation approaches are discussed in Kezirian "*Comparison of the IntraLase femtosecond laser and mechanical keratomes for laser in situ keratomileusis*" J. Cataract Refract. Surg. 30(4):804-811 (2004); Porter "*Separate Effects of the Microkeratome Incision and Laser Ablation on the Eye's Wave Aberration*" Am. J. Ophtalmology, 136(2):327-337 (2003); Pallikaris "*Induced optical aberrations following formation of a laser in situ keratomileusis flap*" J. Cataract Refract. Surg. 28(10): 1737-1741 (2002); Durrie "*Femtosecond laser versus* mechanical keratome flaps in wavefront-guided in situ keratomileusis: prospective contralateral eye study" J. Cataract Refract. Surg. 31(1):120-126 (2005); and Tran "*Randomized prospective clinical study comparing induced aberrations with IntraLase and Hansatome flap creation in fellow eyes: potential impact on wavefront-guided laser in situ keratomileusis*" J. Cataract Refract. Surg. 31(1), 2005, pp. 97-105 (2005). The content of each of the above references is incorporated herein by reference.

The formation of a corneal flap can induce changes in corneal refraction as well as in high-order aberrations, including spherical aberration (SA), coma, trefoil, or the like. These aberrations can affect the treatment outcome and can be taken into account for treatment planning According to some embodiments, deconvolution techniques involve the removal or reduction of surgically induced aberrations, such as spherical aberration induced during LASIK treatment.

A flap induced aberration can be measured directly, in a procedure where the flap is created and placed back into position, but no ablation is performed. For example, aberration changes following a corneal flap creation procedure have been observed in some instances, where the created flap was placed back with no ablation (e.g. no volumetric sculpting) performed.

A flap induced aberration can also be estimated using statistical techniques. For instance, a trend line that represents induced spherical aberration SA (e.g. corresponding to post-operative aberration) vs. pre-operative spherical equivalent SE (e.g. corresponding to ablation magnitude) typically crosses the axis SE=0 at some non-zero level, $SA_0$. This $SA_0$ value quantifies the change in SA when no ablation (e.g. no volumetric sculpting) is performed (e.g. where only the flap is created).

Optionally, the flap induced aberrations may be derived from a flap-creation model, which takes into account site-specific parameters. According to some embodiments, evaluation of flap induced SA may involve an analysis of data associated with different treatment site locations, different surgeons or surgeon techniques, different treatment site conditions (e.g. humidity or temperature), and the like. For example, with regard to surgeon data, evaluation of flap induced SA may involve an analysis of various surgical parameters which impact the cutting of the flap or drying of the corneal stroma. Such data or factors can contribute to the inference of the flap induced SA. Hence, parameters which may impact flap induced aberrations encompass site-specific parameters, surgeon-specific parameters, and refraction-specific parameters. Exemplary refraction-specific parameters include myopia parameters, hyperopia parameters, and mixed astigmatism parameters, for example.

The value of $SA_0$ may depend on multiple factors, including the difference for the flap creation with mechanical microkeratome vs. femtosecond laser, individual surgeon technique, operating environment, refractive type, or the like. Additional aspects of flap related effects which can be used in embodiments of the present invention are discussed in U.S. patent application Ser. No. 13/554,276 filed Jul. 20, 2012, the content of which is incorporated herein by reference.

Figure 4:
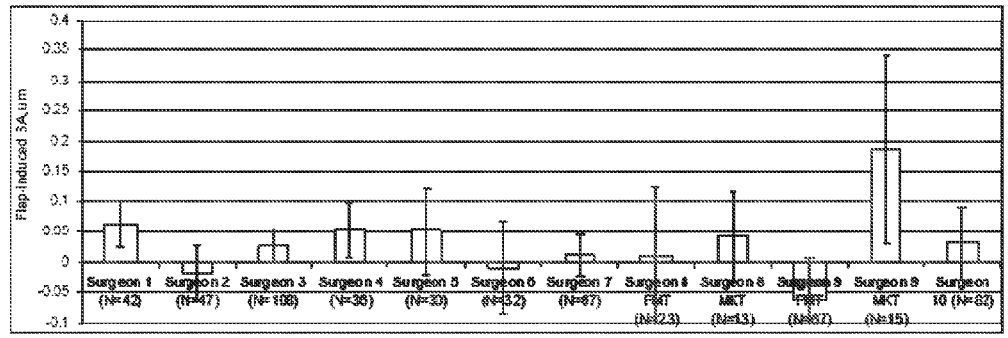
FIG. 4 shows statistical information related to flap-induced spherical aberration, according to embodiments of the present invention.

FIG. 4 provides statistical information related to flap-induced SA calculated with data from controlled clinical studies showing significant differences between different surgeons. As shown here, different surgeons are associated with different amounts of flap induced SA.

Figure 5:
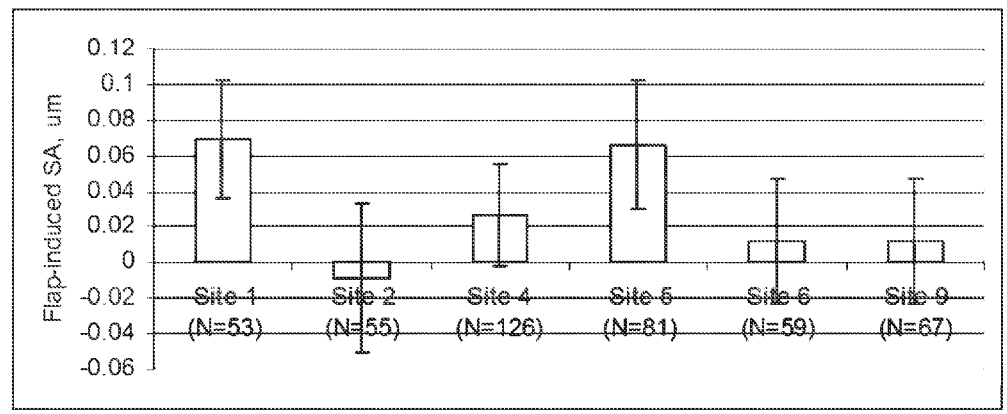
FIG. 5 shows statistical information related to flap-induced spherical aberration, according to embodiments of the present invention.

FIG. 5 provides statistical information related to flap-induced SA calculated with data from controlled clinical studies showing significant differences between different operating sites. As shown here, different operating sites are associated with different amounts of flap induced SA.

Figure 6:
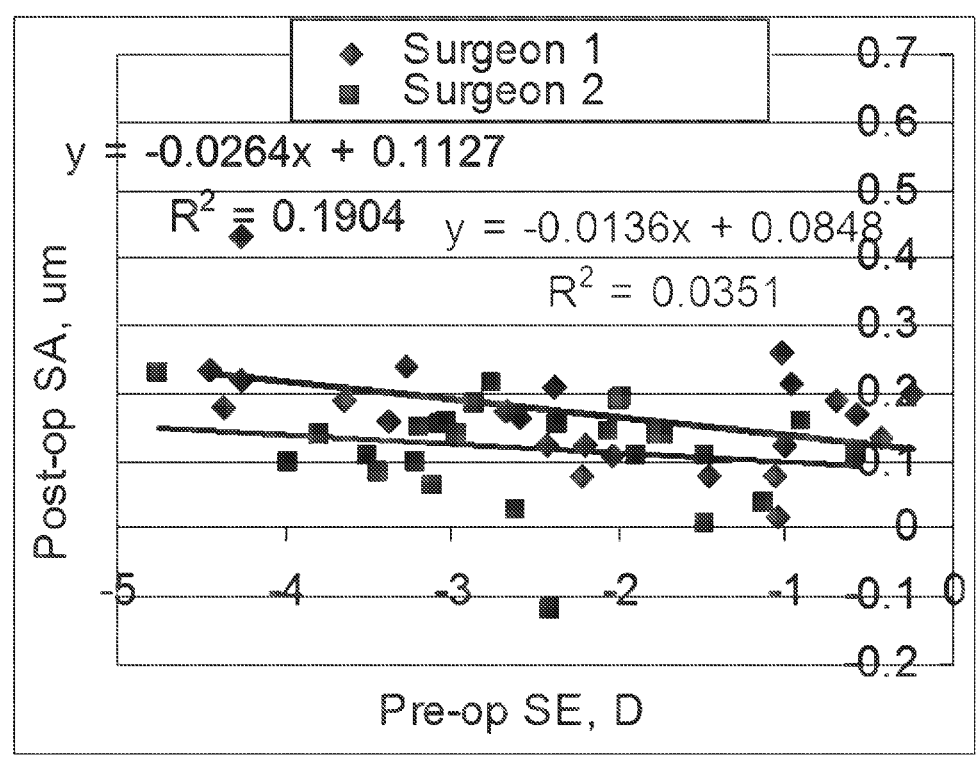
FIG. 6 depicts relationships between post-operative spherical aberration and pre-operative spherical equivalent, according to embodiments of the present invention.
Figure 7:
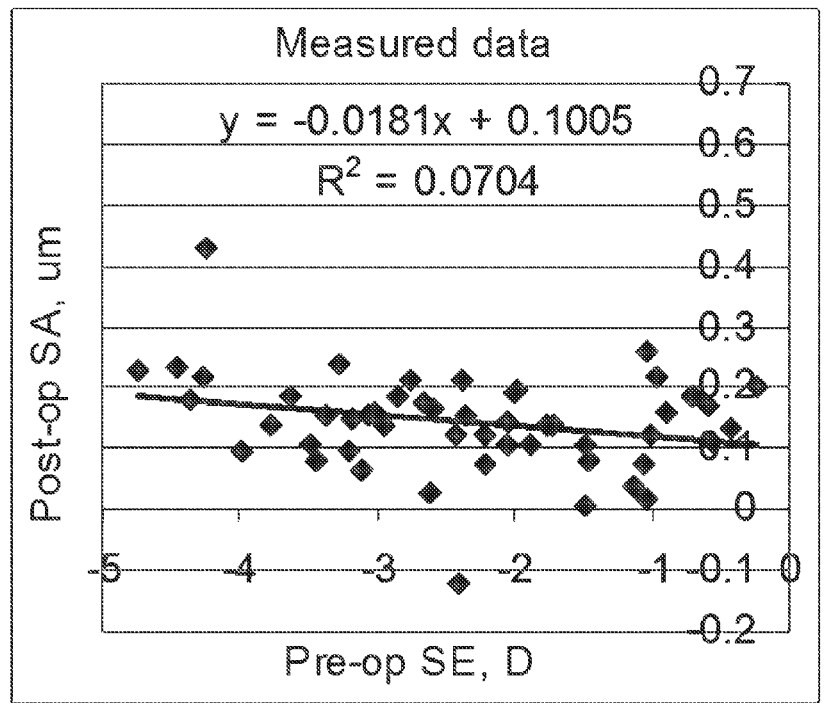
FIG. 7 depicts relations between post-operative spherical aberration and pre-operative spherical equivalent, according to embodiments of the present invention.
Figure 8:
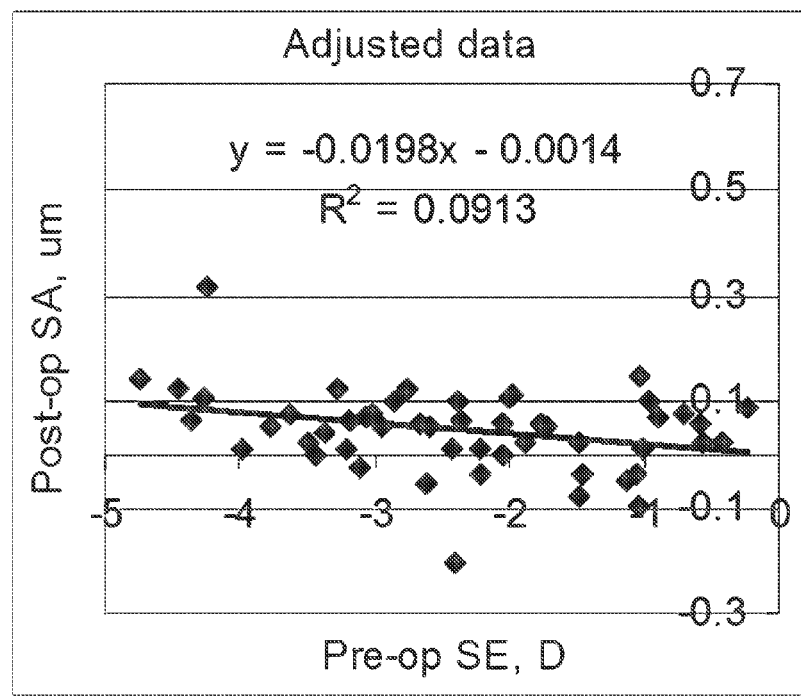
FIG. 8 depicts relations between post-operative spherical aberration and pre-operative spherical equivalent, according to embodiments of the present invention.

Flap-induced aberrations may be taken into account during the treatment planning, where treatment target adjustment is applied to compensate for these aberrations. The adjustments may be derived statistically for each site or surgeon, as illustrated in FIGS. 6, 7, and 8. As shown in these graphs, induced SA can be represented as a function of preoperative SE, in a scalar plot. Depending on the choice of microkeratome and individual surgeon technique, the flap-induced aberrations may differ from site to site or surgeon to surgeon.

FIG. 6 depicts induced SA (y axis) vs. pre-op SE (x axis) trend lines for two surgeons. As shown here, the trend lines cross the y-axis (no ablation) at different levels, which means the flap induced change is different for these two surgeons. Surgeon 1 and 2 from FIG. 6 the same individuals as surgeon 1 and 2 from FIG. 4.

FIG. 7 depicts an induced SA (y axis) vs. pre-op SE (x axis) trend line regression for measured SA data. Hence, it is possible to observe from a cloud plot with preoperative spherical equivalent refraction, where a slope or regression line does not go through zero, that even with zero correction and zero ablation, there is induced SA, and this can be attributed to the flap. FIG. 7 shows data for both surgeons 1 and 2 (from FIG. 6) combined.

FIG. 8 depicts an induced SA (y axis) vs. pre-op SE (x axis) trend line regression for the data adjusted by the surgeon-specific $SA_0$. Hence, it is possible to observe site specific clouds with associated trend/regression lines having different elevations, which show a flap induced effect, and that clouds can be readjusted to set the elevation at zero, with a resulting tighter cloud. As such, when the flap-induced effect is removed, the spread of points is narrowed. The pre-treatment measured wavefront can be adjusted, and the treatment planning can be based on the adjusted data.

The site-specific $SA_0$ can be readjusted such that the adjusted scatter plot will become more compact with increased correlation and $R^2$ values (e.g. compare FIGS. 7 and 8). This allows a better fit for the nomogram adjustment as well as more precise modeling of the cornea healing. The pre-treatment measured wavefront can be adjusted, and the treatment planning can be based on the adjusted data.

Hence, flap-induced aberrations for LASIK treatments may substantially contribute to the surgery outcome. The magnitude of aberrations may be different for different surgeons, sites, or tools, and can be estimated for each surgeon individually. Data for different surgeons may be combined for subsequent analysis and adjustments. The pre-treatment measured wavefront can be adjusted, and the treatment planning can be based on the adjusted data.

In this way, a trend line of post-operative induced SA vs. pre-operative SE can be derived from statistical analysis of treatment data. The level $SA_0$, which the trend line crosses the axis SE=0 signifies the flap-induced SA value (e.g. see FIG. 6). With increasing number of patients this value may be estimated with higher accuracy. Then the treatment target may be adjusted to compensate for the flap-induced SA. This shall reduce the total post-operative induced SA, which will improve the surgery outcome.

Embodiments of the present invention encompass treatment systems and methods that generate or deliver treatment protocols based on flap-induced aberrations. For example, a treatment target can be generated or adjusted to compensate for such induced aberrations. In some instances, treatment targets or treatment target adjustments can be based on factors that are statistically derived for a particular site, surgeon, tool, or the like. Treatment targets or treatment target adjustments can also be based on a flap-creation model, which takes into account site specific parameters.

According to some embodiments, site-specific effects can be compensated for the optimization of a low-pass filtering model for the reduction of post-operative spherical aberration. For example, this site-specific $SA_0$ can be readjusted such that the adjusted scatter plot will become more compact with increased correlation variance and p-values. This provides a good fit for the optimization as well as the choice of the parameters in the model.

In addition to spherical aberration, other flap induced aberrations can be evaluated. Such aberrations may include low order and/or high order aberrations. Induced SE, coma, and trefoil, as non-limiting examples, can also be assessed using statistical trend analysis. Appropriate target adjustments may be also applied to compensate for these aberrations. Table 1 below depicts low order and high order aberration information, corresponding to Zernike polynomials up to the fourth order.

TABLE 1

| i | n | m | Zernike polynomials | Name |
|---|---|---|---|---|
| 0 | 0 | 0 | 1 | piston |
| 1 | 1 | −1 | $2\rho \sin \theta$ | y-tilt |
| 2 | 1 | 1 | $2\rho \cos \theta$ | x-tilt |
| 3 | 2 | −2 | $\sqrt{6}\rho^2 \sin 2\theta$ | y-astigmatism |
| 4 | 2 | 0 | $\sqrt{3}(2\rho^2 - 1)$ | defocus |
| 5 | 2 | 2 | $\sqrt{6}\rho^2 \cos 2\theta$ | x-astigmatism |
| 6 | 3 | −3 | $\sqrt{8}\rho^3 \sin 3\theta$ | y-trefoil |
| 7 | 3 | −1 | $\sqrt{8}(3\rho^3 - 2\rho) \sin \theta$ | y-coma |
| 8 | 3 | 1 | $\sqrt{8}(3\rho^3 - 2\rho) \cos \theta$ | x-coma |
| 9 | 3 | 3 | $\sqrt{8}\rho^3 \cos 3\theta$ | x-trefoil |
| 10 | 4 | −4 | $\sqrt{10}\rho^4 \sin 4\theta$ | y-quadrafoil |
| 11 | 4 | −2 | $\sqrt{10}(4\rho^4 - 3\rho^2) \sin 2\theta$ | y-secondary astigmatism |
| 12 | 4 | 0 | $\sqrt{5}(6\rho^4 - 6\rho^2 + 1)$ | spherical aberration |
| 13 | 4 | 2 | $\sqrt{10}(4\rho^4 - 3\rho^2) \cos 2\theta$ | x-secondary astigmatism |
| 14 | 4 | 4 | $\sqrt{10}\rho^4 \cos 4\theta$ | x-quadrafoil |

As shown here, low order aberrations correspond to those polynomials where $n \leq 2$ ($i=Z_{0-5}$), and high order aberrations correspond to those polynomials where $n \geq 3$ ($i=Z_{6-12}$). As shown here, high order polynomials include third order ($n=3$) and fourth order ($n=4$) aberrations. Generally, high order aberrations include third order errors and above.

For example, a method that is based on an unadjusted scatter plot between the intended vs. achieved refractions (e.g. SE) can be modified to take into account a site specific variable (e.g. sphere or SE change), thus providing a precise scatter plot that represents a good fit of the data.

In a similar approach, a sequential estimation technique can be applied to wavefront measurements, performed with an aberrometer, where a lenslet image of distorted spots yields noisy and incomplete data. In addition to or as an alternative to using multiple measurements and Fourier decomposition approaches to reconstruct a wavefront surface, it is possible to use a sequential estimation process to provide a statistically optimal combination of sequential measurements and include a priori information.

Deconvolution

Embodiments of the present invention also encompass refinement of a deconvolution technique in spherical aberration reduction process, which can involve adjusting a site specific effect adjustment on flap induced spherical aberrations to optimize the deconvolution kernel parameters. Hence, it is possible to adjust a plot cloud, by readjusting the piston (the interception of the regression line from different sites or different surgeons, to renormalize it), so as to reduce the amount of standard deviation in the cloud and to make the cloud more compact. Exemplary techniques may involve adjusting the pre-treatment measured wavefront, which then goes in the treatment planning. This can be related to a deconvolution technique for reduced SA. In some cases, it can be useful to adjust the treatment plan to compensate for flap-induced SE, SA, and other flap-induced aberrations. The adjustments may be not exactly equal to measured flap-induced values (e.g. as in FIG. 6) but can take into account the post-operative smoothing. This may be done by de-convolution. Hence, once an $SA_0$ is renormalized from a different site (or surgeon or refractive type), it is possible to obtain a precise single $SA_0$. In turn, this single $SA_0$ can be used to optimize a low pass filtering kernel so the kernel parameters obtained in this way are more precise. In some instances, for $SA_0$, it is a parameter to represent the average flap-cutting induced spherical aberration, among many surgeons (e.g. if data is available). With its use, a more precise optimized linear filter (OLF) can be obtained by fitting to existing clinical data. Hence, a deconvolution technique that is used with the OLF can yield an improved outcome. According to some embodiments, an optimized linear filter can include low pass filtering, and/or filtering that is not low pass. For example, there can be other spatial frequency information that is not low pass The compensation techniques for flap induced aberrations disclosed herein can be used or implemented in conjunction with various deconvolution techniques, such as those described in U.S. Provisional Patent Application No. 61/708,815 filed Oct. 2, 2012, U.S. Provisional Patent Application No. 61/871,120 filed Aug. 28, 2013, and U.S. patent application Ser. No. 14/044,650 filed Oct. 2, 2013. The content of each of these filings is incorporated herein by reference. In some cases, a deconvolution method used to compensate for a healing effect can also be used to compensate for a flap effect.

Low Order Aberrations

Embodiments of the present invention further encompass refinement techniques for low order aberrations such as sphere and cylinder. In some cases, this may involve the use of data to evaluate a relationship between intended and achieved refractions, such as sphere, cylinder, or SE, which is a useful parameter for characterizing the power of the cornea.

For example, it is possible to combine a broad range of clinical data used in one or more trials, which may encompass myopia patients, hyperopia patients, mixed astigmatism patients, and the like, to evaluate intended and achieved refractions. In some situations, an entire cohort may be used, meaning all data from several different clinical trials. For example, it is possible to use WaveScan trials for myopia, for hyperopia, for high myopia, for mixed astigmatism, and for monovision. Therefore, the entire cohort may be considered as a plurality of clinical data sets. A regression line can be assessed on the basis of features of slope, intercept, and the like, to evaluate and/or adjust a treatment plan. For example, if the slope of the regression line is greater than 1, it may be possible to conclude there is an overcorrection, and if the slope is smaller than one, it may be possible to conclude there is an undercorrection. In this way, it is possible to adjust the basis data accordingly, so as to achieve or more closely approach a slope of 1, and an intercept of 0. Exemplary aspects of basis data for use in vision treatment are discussed in U.S. patent application Ser. No. 14/073,583 filed Nov. 6, 2013, the content of which is incorporated herein by reference.

In some instances, data may be classified and analyzed according to specific cohorts. For example, SA data can present different slopes for hyperopia and myopia. Instead of combining data from hyperopia and myopia patients, certain techniques may involve developing one trend or regression line corresponding to hyperopia patient data and another trend or regression line corresponding to myopia patient data. In this way, is it possible to achieve precise nomogram estimates. Such data can be used to readjust basis functions to obtain improved treatment plans. Hence, in addition to site specific or physician specific factors, embodiments of the present invention also encompass the use of treatment type specific factors.

A healing process or low pass filter process (or an optimized linear filter process) can be used to account for tissue changes following surgery, which may affect both high order and low order aberrations. Exemplary treatment target adjustment processes, which can account for flap and/or healing effects, can involve deconvolution techniques, as discussed elsewhere herein. A healing process can be considered to be a convolution process. A deconvolution process is a reverse operation, which can be performed to undo the convolution, or reverse the healing effect. In addition to providing treatment plans or adjustments for obtaining post operative healed refractions that match with desired refractions, embodiments of the present invention also encompass techniques for lowering SA for both high and low order aberrations. According to some embodiments, an optimized linear filter can include low pass filtering, and/or filtering that is not low pass. For example, there can be other spatial frequency information that is not low pass.

In some instances, the data present some degree of spread, which can be evaluated an R square analysis. An R square analysis, as a measure of regression for the variance, may in some instances have a value within a range from about 0.92 to 0.95, or some other value that is less than one so as to indicate a degree of spread. Optionally, adjustments (e.g. per site) can be made to improve the R square analysis, and hence obtain an improved outcome, and the slope may remain at one following adjustment. Such techniques can have a significant effect on hyperopia, where the standard deviation (or the spread) of post-operative data may be highly scattered. In this way, a similar approach can be used for data corresponding to individual sites, and individual regression lines corresponding to respective sites can have unique intercepts. Such data representations can be adjusted, with the R square analysis showing a tighter fit following the adjustment. In some instances, for individual sites there may be an associated systemic shift, where the slope may be the same, and the intercept may be different, for low order aberrations. These results can be used to readjust the scatter, to obtain a tighter fit, so as to improve the eventual treatment outcome.

Figure 9:
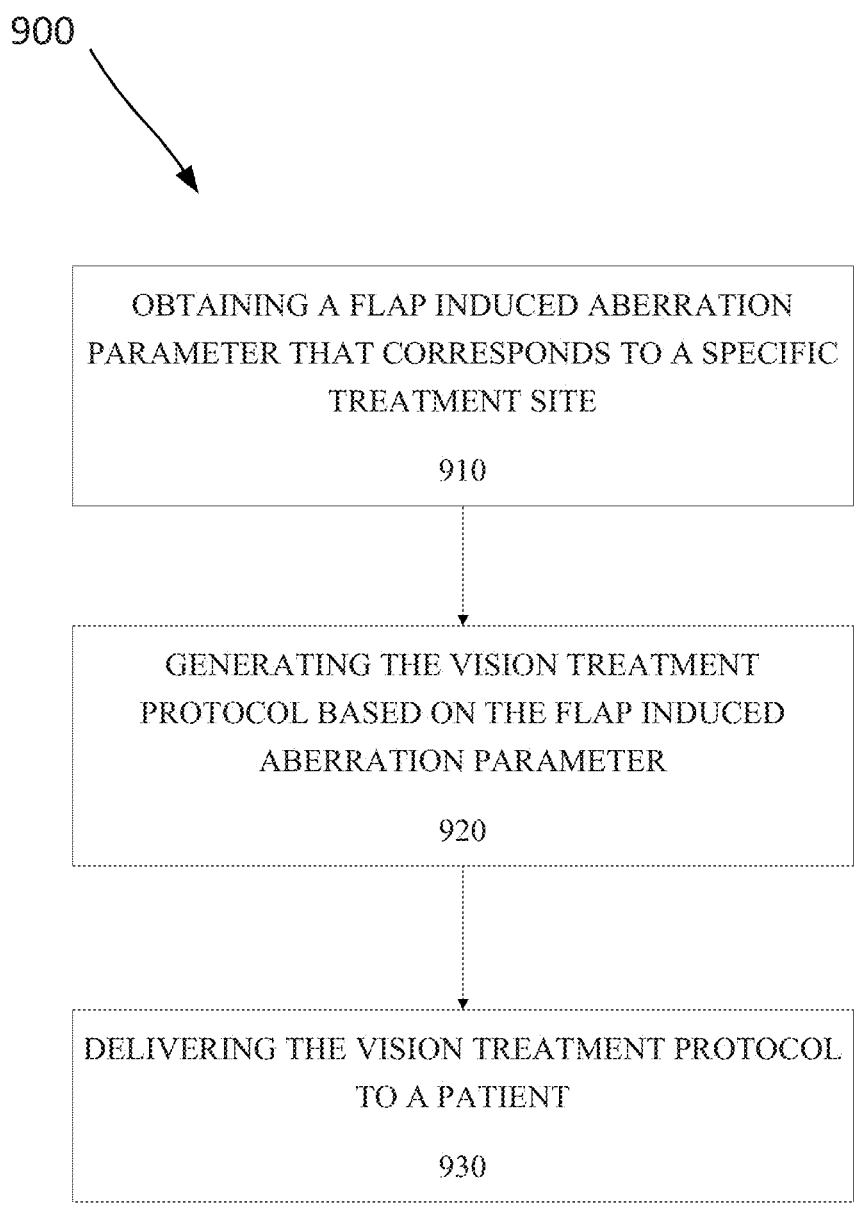
FIG. 9 depicts aspects of techniques for generating a vision treatment protocol, according to embodiments of the present invention.

FIG. 9 depicts aspects of a method 900 of generating a vision treatment protocol for a patient, according to embodiments of the present invention. As shown here, the method includes obtaining a flap induced aberration parameter that corresponds to a specific treatment site, as indicated by step 910. The flap induced aberration parameter can include a high order aberration, such as spherical aberration. Further, the method includes generating the vision treatment protocol based on the flap induced aberration parameter, as indicated by step 920. In some cases, methods may include delivering the vision treatment protocol to a patient, as indicated by step 930.

Figure 10:
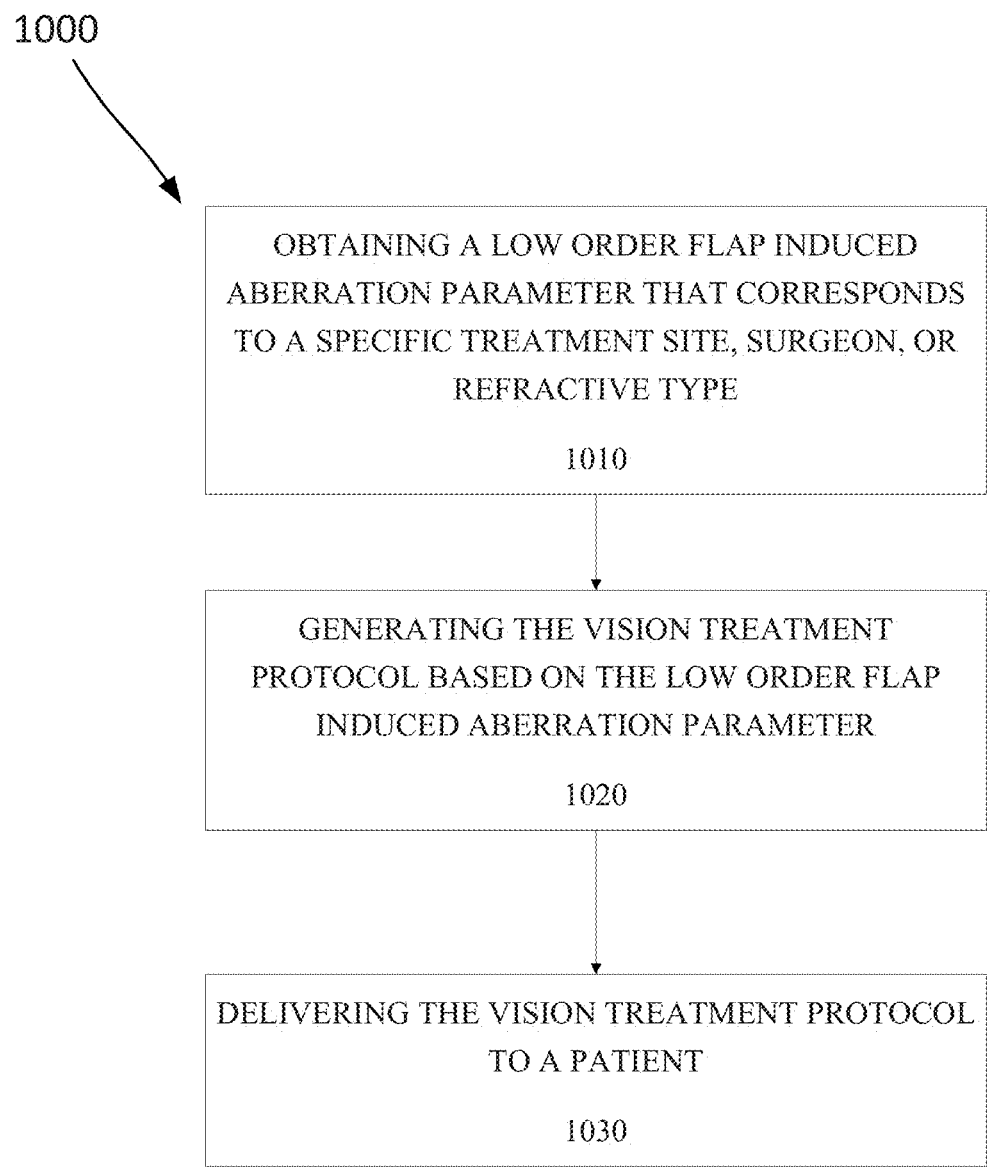
FIG. 10 depicts aspects of techniques for generating a vision treatment protocol, according to embodiments of the present invention.

FIG. 10 depicts aspects of a method 1000 of generating a vision treatment protocol for a patient, according to embodiments of the present invention. As shown here, the method includes obtaining a low order flap induced aberration parameter that corresponds to a specific treatment site, surgeon, or refractive type, as indicated by step 1010. The low order flap induced aberration parameter may include, for example, a spherical equivalent. Further, the method includes generating the vision treatment protocol based on the low order flap induced aberration parameter, as indicated by step 1020. In some cases, methods may include delivering the vision treatment protocol to a patient, as indicated by step 1030.

Figure 11:
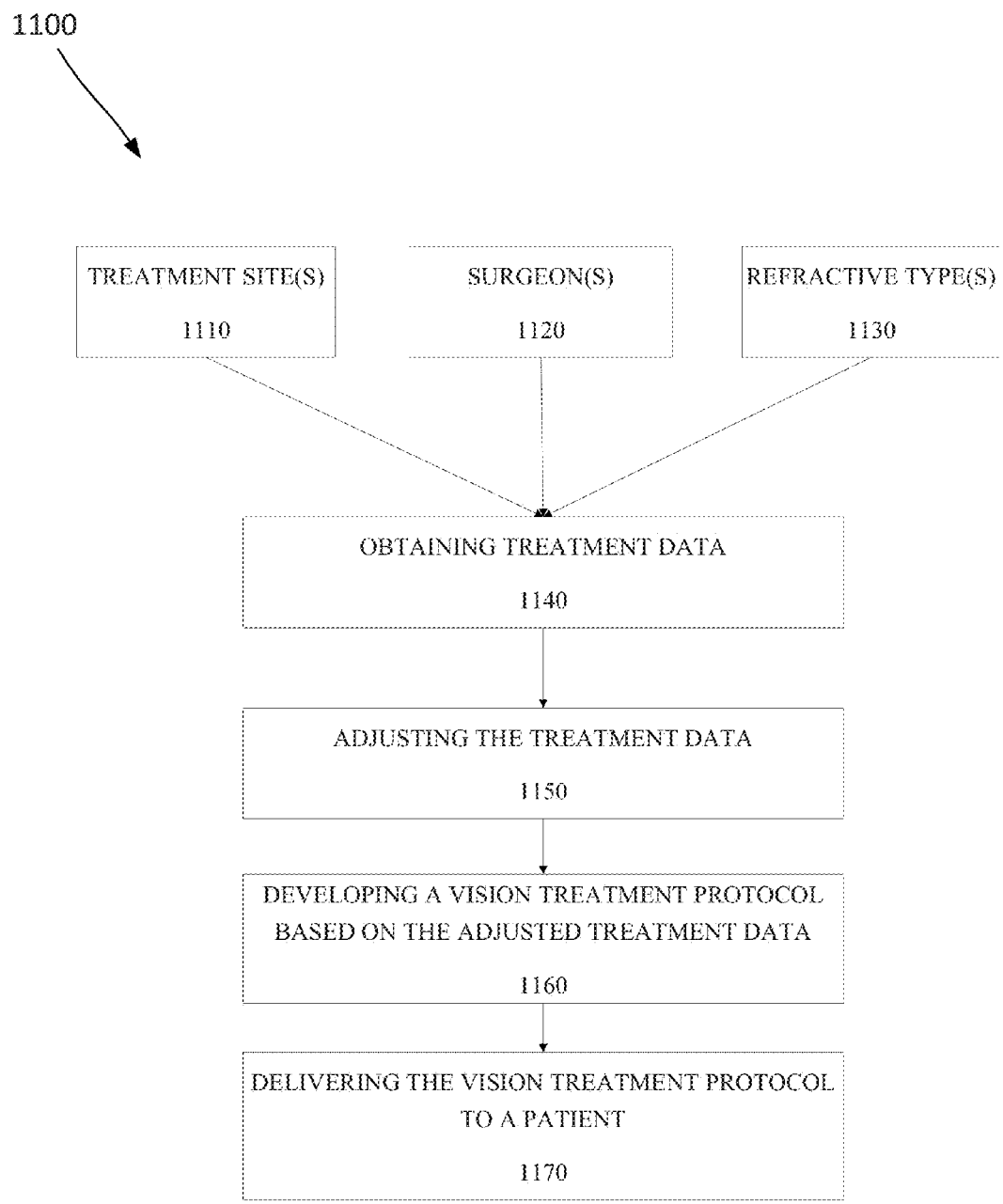
FIG. 11 depicts aspects of techniques for developing a vision treatment protocol, according to embodiments of the present invention.

FIG. 11 depicts aspects of a method 1100 of developing a vision treatment protocol for a patient, according to embodiments of the present invention. As shown here the method includes obtaining treatment data associated with one or more treatment sites 1110, one or more surgeons or operators 1120, and/or one or more refractive types 1130, as indicated by step 1140. Further, the method includes adjusting the treatment data, as indicated by step 1150, and developing the vision treatment protocol based on the adjusted data, as indicated by step 1160. In some cases, methods may include delivering the vision treatment protocol to the patient, as indicated by step 1070.

All patent filings (including patents, patent applications, and patent publications), scientific journals, books, treatises, technical references, and other publications and materials discussed in this application are incorporated herein by reference in their entirety for all purposes.

A variety of modifications are possible within the scope of the present invention. A variety of parameters, variables, factors, and the like can be incorporated into the exemplary method steps or system modules. While the specific embodiments have been described in some detail, by way of example and for clarity of understanding, a variety of adaptations, changes, and modifications will be obvious to those of skill in the art. Although the invention has been described with specific reference to a wavefront system using lenslets, other suitable wavefront systems that measure angles of light passing through the eye may be employed. For example, systems using the principles of ray tracing aberrometry, tscherning aberrometry, and dynamic skiascopy may be used with the current invention. The above systems are available from TRACEY Technologies of Bellaire, Tex., Wavelight of Erlangen, Germany, and Nidek, Inc. of Fremont, Calif., respectively. The invention may also be practiced with a spatially resolved refractometer as described in U.S. Pat. Nos. 6,099,125; 6,000,800; and 5,258,791, the full disclosures of which are incorporated herein by reference. Treatments that may benefit from the invention include intraocular lenses, contact lenses, spectacles and other surgical methods in addition to refractive laser corneal surgery.

Each of the calculations or operations discussed herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like. While the exemplary embodiments have been described in some detail, by way of example and for clarity of understanding, those of skill in the art will recognize that a variety of modification, adaptations, and changes may be employed.

The methods and apparatuses of the present invention may be provided in one or more kits for such use. The kits may comprise a system for determining a treatment for an eye of a patient, and instructions for use. Optionally, such kits may further include any of the other system components described in relation to the present invention and any other materials or items relevant to the present invention. The instructions for use can set forth any of the methods as described herein.

While the above provides a full and complete disclosure of exemplary embodiments of the present invention, various modifications, alternate constructions and equivalents may be employed as desired. Consequently, although the embodiments have been described in some detail, by way of example and for clarity of understanding, a variety of modifications, changes, and adaptations will be obvious to those of skill in the art. Accordingly, the above description and illustrations should not be construed as limiting the invention, which can be defined by the claims.

What is claimed is:

1. A method of generating a vision treatment protocol for a patient, the method executed by a computer system, the method comprising:
   statistically deriving, from a set of clinical study data, a flap induced aberration parameter, the statistically deriving including:
      obtaining, from the set of clinical study data, a set of data that includes data points linking induced spherical aberration values that correspond to post-operative aberration to pre-operative spherical equivalent values that correspond to ablation magnitude, and
      deriving, from the set of data, a spherical-aberration-zero value that quantifies change in spherical aberration when no volumetric sculpting is performed, the spherical-aberration-zero value comprising the flap induced aberration parameter, the spherical-aberration-zero value comprising the change in spherical aberration when no volumetric sculpting is performed but a flap is created;
   generating the vision treatment protocol with the computer system, wherein the computer system comprises a processor and a tangible non-transitory computer readable medium, and wherein the computer readable medium is programmed with a computer application that, when executed by the processor, causes the processor to generate the vision treatment protocol based on the flap induced aberration parameter by generating the vision treatment protocol based on a treatment target that is adjusted based on the spherical-aberration-zero value, the treatment target comprising a desired effect to be delivered to the cornea;
   creating a corneal flap in an eye of the patient; and
   delivering the vision treatment protocol to the eye of the patient, wherein the vision treatment protocol comprises a laser treatment.

2. The method according to claim 1, wherein the flap induced aberration parameter comprises a high order aberration.

3. The method according to claim 2, wherein the high order aberration comprises a spherical aberration.

4. A system for generating a vision treatment protocol for a patient, comprising:
   a processor;
   a first module comprising a tangible medium embodying machine-readable code executed on the processor to obtain a flap induced aberration parameter by:
      statistically deriving, from a set of clinical study data, a flap induced aberration parameter, the statistically deriving including:
         obtaining, from the set of clinical study data, a set of data that includes data points linking induced spherical aberration values that correspond to post-operative aberration to pre-operative spherical equivalent values that correspond to ablation magnitude, and
         deriving, from the set of data, a spherical-aberration-zero value that quantifies change in spherical aberration when no volumetric sculpting is performed, the spherical-aberration-zero value comprising the flap induced aberration parameter, the spherical-aberration-zero value comprising the change in spherical aberration when no volumetric sculpting is performed but a flap is created;
   a second module comprising a tangible medium embodying machine-readable code executed on the processor to:
      generate the vision treatment protocol based on the flap induced aberration parameter by:
         generating the vision treatment protocol based on a treatment target that is adjusted based on the spherical-aberration-zero value, the treatment target comprising a desired effect to be delivered to the cornea; and
   a vision treatment protocol delivery module comprising a tangible medium embodying machine-readable code executed on the processor to:
      create a corneal flap in an eye of the patient; and
      deliver the vision treatment protocol to the eye of the patient, wherein the vision treatment protocol comprises a laser treatment.

5. The system according to claim 4, wherein the flap induced aberration parameter comprises a high order aberration.

6. The system according to claim 5, wherein the high order aberration comprises a spherical aberration.

7. A computer product embodied on a tangible computer readable storage medium, comprising:
   code for obtaining a flap induced aberration parameter by:
      statistically deriving, from a set of clinical study data, a flap induced aberration parameter, the statistically deriving including:
         obtaining, from the set of clinical study data, a set of data that includes data points linking induced spherical aberration values that correspond to post-operative aberration to pre-operative spherical equivalent values that correspond to ablation magnitude, and
         deriving, from the set of data, a spherical-aberration-zero value that quantifies change in spherical aberration when no volumetric sculpting is performed, the spherical-aberration-zero value comprising the flap induced aberration parameter, the spherical-aberration-zero value comprising the change in spherical aberration when no volumetric sculpting is performed but a flap is created;

code for generating the vision treatment protocol based on the flap induced aberration parameter by generating the vision treatment protocol based on a treatment target that is adjusted based on the spherical-aberration-zero value, the treatment target comprising a desired effect to be delivered to the cornea; and code for delivering a vision treatment protocol by:
creating a corneal flap in an eye of the patient; and
delivering the vision treatment protocol to the eye of the patient, wherein the vision treatment protocol comprises a laser treatment.

8. The method according to claim 1, wherein the step of creating the cornel flap in the eye of the patient comprises creating the corneal flap with a microkeratome.

9. The method of claim 1, wherein deriving, from the set of data, the spherical-aberration-zero value comprises generating a trend line of post-operative induced spherical aberration versus pre-operative spherical equivalent values, based on the set of data that includes the data points linking induced spherical aberration values to pre-operative spherical equivalent values, and determining, as the spherical-aberration-zero value, the spherical aberration value at the point that the trend line crosses zero for spherical equivalent.

10. The system of claim 4, wherein deriving, from the set of data, the spherical-aberration-zero value comprises generating a trend line of post-operative induced spherical aberration versus pre-operative spherical equivalent values, based on the set of data that includes the data points linking induced spherical aberration values to pre-operative spherical equivalent values, and determining, as the spherical-aberration-zero value, the spherical aberration value at the point that the trend line crosses zero for spherical equivalent.

11. The computer product of claim 7, wherein deriving, from the set of data, the spherical-aberration-zero value comprises generating a trend line of post-operative induced spherical aberration versus pre-operative spherical equivalent values, based on the set of data that includes the data points linking induced spherical aberration values to pre-operative spherical equivalent values, and determining, as the spherical-aberration-zero value, the spherical aberration value at the point that the trend line crosses zero for spherical equivalent.

* * * * *